(12) United States Patent
Zhang et al.

(10) Patent No.: US 11,440,940 B2
(45) Date of Patent: Sep. 13, 2022

(54) POLYMYXIN B COMPONENT OR SALT THEREOF, AND PREPARATION AND APPLICATION THEREOF

(71) Applicant: SPH NO.1 BIOCHEMICAL & PHARMACEUTICAL CO.,LTD., Shanghai (CN)

(72) Inventors: Hanzhi Zhang, Shanghai (CN); Hao Liu, Shanghai (CN); Zhenhui Huang, Shanghai (CN); Ning Sun, Shanghai (CN); Wenyan Luo, Shanghai (CN); Jinguo Ding, Shanghai (CN); Xiaofen Liu, Shanghai (CN); Xingchen Bian, Shanghai (CN)

(73) Assignee: SPH NO. 1 BIOCHEMICAL & PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 17/187,708

(22) Filed: Feb. 26, 2021

(65) Prior Publication Data
US 2021/0206807 A1 Jul. 8, 2021

Related U.S. Application Data

(63) Continuation of application No. PCT/CN2020/131148, filed on Nov. 24, 2020.

(30) Foreign Application Priority Data

Jan. 2, 2020 (CN) .......................... 202010001700.8

(51) Int. Cl.
*C07K 7/62* (2006.01)
*C07K 1/16* (2006.01)
*A61K 38/00* (2006.01)

(52) U.S. Cl.
CPC .................. *C07K 7/62* (2013.01); *C07K 1/16* (2013.01); *A61K 38/00* (2013.01)

(58) Field of Classification Search
CPC .................................... A61K 38/12; C07K 7/62
See application file for complete search history.

(56) References Cited

U.S. PATENT DOCUMENTS

| 7,935,503 B2 * | 5/2011 | Doran-Peterson ...... C12P 21/02 435/71.3 |
| 2007/0009960 A1 * | 1/2007 | Schafer ................ G01N 33/533 435/7.1 |

FOREIGN PATENT DOCUMENTS

| CN | 104086633 A | 10/2014 |
| CN | 107367562 A | 11/2017 |

(Continued)

OTHER PUBLICATIONS

Orwa et al. Isolation and structural characterization of polymyxin B components. Journal of Chromatography A. 2001, vol. 912, pp. 369-373. (Year: 2001).*

(Continued)

*Primary Examiner* — Jeffrey E. Russel (57) ABSTRACT

A polymyxin B component or salts thereof, and a preparation and application thereof. The polymyxin B component includes six α,γ-diaminobutyric acids respectively at positions 1, 3-5 and 8-9, two threonine residues at positions 2 and 10, a phenylalanine residue at position 6 and a leucine residue at position 7 linked in sequence. The threonine residue at position 10 is linked to the α,γ-diaminobutyric acid at position 4 by an amido bond, and the α,γ-diaminobutyric acid at position 1 is linked to 6-methyloctyl-2-enoyl.

6 Claims, 6 Drawing Sheets

(56) References Cited

FOREIGN PATENT DOCUMENTS

| | | |
|---|---|---|
| CN | 108350034 A | 7/2018 |
| CN | 109206486 A | 1/2019 |
| CN | 110845579 A | 2/2020 |
| CN | 111072757 A | 4/2020 |

OTHER PUBLICATIONS

Zavascki et al. Polymyxin B for the treatment of multidrug-resistant pathogens: a critical review. Journal of Antimicrobial Chemotherapy. 2007, vol. 60, pp. 1206-1215. (Year: 2007).*

Tony Velkov, Philip E. Thompson, Roger L. Nation and Jian Li; Structure-Activity Relationships of Polymyxin Antibiotics; Oct. 29, 2009; School of Medicine, Deakin University, Pigdons Road, Geelong 3217, Victoria, Australia.

Zhang, Hanzhi et al.; Identification of unknown Impurities in Polymyxin B Sulfate by HPLC-MS/MS; Shanghai Institute of Food and Drug Control, Jun. 30, 2018, vol. 11, p. 918-924.

Zhang, Hanzhi et al.; Identification of unknown Impurities in Polymyxin B Sulfate via HPLC-MS/MS and photochemical reaction, (2018).

The Contribution of the N-Terminal Structure of Polymyxin B Peptides to Antimicrobial and Lipopolysaccharide Binding Activity, Bull. Chem. Soc. Jpn., Sep. 10, 2004; vol. 77, p. 1915-1924.

* cited by examiner

POLYMYXIN B COMPONENT OR SALT THEREOF, AND PREPARATION AND APPLICATION THEREOF

CROSS-REFERENCE TO RELATED APPLICATIONS

This application is a continuation of International Patent Application No. PCT/CN2020/131148, filed on Nov. 24, 2020, which claims the benefit of priority from Chinese Patent Application No. 202010001700.8, filed on Jan. 2, 2020.

TECHNICAL FIELD

This application relates to pharmaceutical chemistry, and more particularly to a polymyxin B component or a salt thereof, and a preparation and application thereof.

BACKGROUND

Polymyxin B is a cyclic lipopeptide antibiotic, which has a potent bactericidal effect on Gram negative bacilli. Clinically, the polymyxin B is commonly used in the form of polymyxin B sulfate, which is regarded as the last defense for the treatment of multidrug-resistant Gram-negative bacilli.

Polymyxin B is a mixture of a series of structurally similar cyclic lipopeptides produced by fermentation. The polymyxin B mainly includes known polymyxins B1, B2, B3 and B1-I and other unidentified components, where the polymyxins B1 and B2 have biological activity, and the polymyxins B3 and B1-I are the major impurities. These polymyxin components have the same skeleton structure and vary only in the substituent. A structural formula of the polymyxin B1 is shown as follows:

in which N-terminal fatty acyl chain (6'R-methyloctanoyl), six L-α,γ-diaminobutyric acids (respectively in positions 1, 3-5 and 8-9), two L-threonine residues (respectively positions 2 and 10), D-phenylalanine in position 6 and L-leucine in position 7 are successively linked through an amide bond, and the L-α,γ-diaminobutyric acids in positions 4 and 5 and the L-threonine residue in position 10 are linked through an amide bond to form a cyclic heptapeptide.

Given the above, it is of great significance to perform isolation and characterization on chemical components of polymyxin B.

SUMMARY

An object of this application is to provide a polymyxin B component or salts thereof, and a preparation and application thereof. This application isolates a novel component with strong antibacterial activity from the polymyxin B and characterizes the same.

Technical solutions of this application are described as follows.

In a first, this application provides a polymyxin B component (also called 2',3'-dehydropolymyxin B1 hereinafter) or a salt thereof, comprising: α,γ-diaminobutyric acids at positions 1, 3-5 and 8-9, threonine residues at positions 2 and 10, a phenylalanine residue at position 6 and a leucine residue at position 7 successively linked;

wherein the threonine residue at position 10 is linked to the α,γ-diaminobutyric acid at position 4 through an amido bond; and the α,γ-diaminobutyric acid at position 1 is linked to 6-methyloctyl-2-enoyl.

In an embodiment, the 6-methyloctyl-2-enoyl is (R,E)-6-methyloctyl-2-enoyl, (R,Z)-6-methyloctyl-2-enoyl, or an enantiomer thereof, preferably (R,E)-6-methyloctyl-2-enoyl.

In an embodiment, an α-amino of the α,γ-diaminobutyric acid at position 1 is linked to the 6-methyloctyl-2-enoyl; and/or an α-amino of the α,γ-diaminobutyric acid at position 4 is linked to a carboxyl of the α,γ-diaminobutyric acid at position 3 through an amido bond, and a γ-amino of the α,γ-diaminobutyric acid at position 4 is linked to a carboxyl of the threonine residue at position 10 through an amido bond; and/or the salt of the polymyxin B component is a polymyxin B sulfate.

In an embodiment, the α-amino of the α,γ-diaminobutyric acid at position 1 is linked to (R,E)-6-methyloctyl-2-enoyl or (R,Z)-6-methyloctyl-2-enoyl.

In an embodiment, the polymyxin B component is a compound of formula (I) or an enantiomer thereof.

In an embodiment, the polymyxin B component is isolated from polymyxin B or a salt thereof. In an embodiment, the polymyxin B component is isolated from polymyxin B sulfate, where the polymyxin B sulfate is preferably purchased from Shanghai Pharma No. 1 Biochemical & Pharmaceutical Co., Ltd with batch No. 1512802.

In an embodiment, the polymyxin B component has a molecular weight of 1200.73-1200.75.

In an embodiment, the isolation of the polymyxin B component from the polymyxin B or a salt thereof is performed by preparative liquid chromatography.

In an embodiment, a chromatographic column used in the preparative liquid chromatography is a C18 column.

In an embodiment, a mobile phase used in the preparative liquid chromatography is a mixture of an aqueous formic acid solution and acetonitrile, where a volume percentage of formic acid in the aqueous formic acid solution is greater than 0 and less than or equal to 10%, preferably 0.01%-10%, and more preferably 0.1%

In an embodiment, a volume ratio of the aqueous formic acid solution to acetonitrile is (99-1):1, preferably 85:15.

In an embodiment, a flow rate of the mobile phase is 5-20 mL/min, preferably 15 mL/min; an injection volume is 50-1000 μL, preferably 500 μL; and a detection wavelength is 190-400 nm, preferably 215 nm.

In an embodiment, individual fractions separated by the preparative liquid chromatography are detected by electrospray ionization-mass spectrometry (ESI-MS) and the polymyxin B component of interest is collected.

In an embodiment, the ESI-MS is performed in a positive ion mode with a scanning range (m/z) of 50-3200, preferably 100-1250.

In a second aspect, this application also provides a method for preparing a polymyxin B component or a salt thereof, comprising:

(1) isolating the polymyxin B component from polymyxin B or a salt thereof, wherein a molecular formula of the polymyxin B component is $CH_{56}N_{16}O_{13}$; and (2) subjecting the polymyxin B component to salt formation with an acid to produce the salt of the polymyxin B component.

In an embodiment, the acid can be any commonly-used acid in the art as long as it can react with the polymyxin B component to form the corresponding salt, preferably sulfuric acid; and the salt of the polymyxin B component is a sulfate of the polymyxin B component.

In an embodiment, the polymyxin B component is isolated from the polymyxin B or a salt thereof by preparative liquid chromatography.

In an embodiment, a chromatographic column used in the preparative liquid chromatography is a C18 column.

In an embodiment, a mobile phase used in the preparative liquid chromatography is a mixture of an aqueous formic acid solution and acetonitrile, where a volume percentage of formic acid in the aqueous formic acid solution is greater than 0 and less than or equal to 10%, preferably 0.01%-10%, and more preferably 0.1%.

In an embodiment, a volume ratio of the aqueous formic acid solution to acetonitrile is (99-1):1, preferably 85:15.

In an embodiment, a flow rate of the mobile phase is 5-20 mL/min, preferably 15 mL/min, an injection volume is 50-1000 μL, preferably 500 μL; and a detection wavelength is 190400 nm, preferably 215 nm.

In an embodiment, the polymyxin B or the salt thereof was first dissolved with a mixture of water and acetonitrile in a volume ratio of 80:20 to a concentration of 10 mg/mL.

In an embodiment, individual fractions separated by the preparative liquid chromatography are detected by the ESI-MS and the polymyxin B component of interest is collected.

In an embodiment, the ESI-MS is performed in a positive ion mode with a scanning range (m/z) of 50-3200, preferably 100-1250.

In an embodiment, the polymyxin B component is characterized by high performance liquid chromatography-mass spectrometry (HPLC-MS) and nuclear magnetic resonance (NMR).

In an embodiment, a chromatographic column used in the HPLC-MS is a C18 column.

In an embodiment, a mobile phase used in the HPLC-MS is a mixture of an aqueous trifluoroacetic acid and acetonitrile, where a volume percentage of trifluoroacetic acid in the aqueous trifluoroacetic acid solution is greater than 0 and less than or equal 10%, preferably 0.01-10%, and more preferably 0.1%.

In an embodiment, a volume ratio of the aqueous trifluoroacetic acid solution to acetonitrile is (99-1):1, preferably 80:20.

In an embodiment, a flow rate of the mobile phase the HPLC-MS is 0.1-2 mL/min, preferably 1 mL/min, an injection volume is 50-1000 μL, preferably 20 μL, and a detection wavelength is 190-400 nm, preferably 215 nm.

In an embodiment, an ionization method used in the HPLC-MS is electrospray ionization or atmospheric pressure ionization.

In an embodiment, a mass analyzer used in the HPLC-MS is a quadrupole time-of-flight mass spectrometer (Q-TOF), a linear ion trap mass spectrometer, a three dimensional ion trap mass spectrometer, a triple-quadrupole mass spectrometer or an orbitrap mass spectrometer.

In an embodiment, the polymyxin B component is characterized based on information from primary mass spectrum and secondary mass spectrum.

In an embodiment, the primary mass spectrum and the secondary mass spectrum both have a scanning range (m/z) of 50-2000.

In an embodiment, collision energy of the secondary mass spectrum is 10-30 eV.

In an embodiment, a scanning frequency of the NMR is 300-800 MHz, preferably 500 MHz.

In a third aspect, this application further provides a polymyxin B component or a salt thereof prepared by the above method.

In a fourth aspect, this application also provides a pharmaceutical composition, comprising the above-mentioned polymyxin B component or a salt thereof.

In an embodiment, the pharmaceutical composition is in a form of injection or ointment.

In a fifth aspect, this application also provides a method of treating bacterial infection in a subject in need thereof, comprising:

administering a therapeutically effective amount of the above-mentioned polymyxin B component or a salt thereof to the subject;

wherein the bacterial infection is caused by a gram-negative bacterium.

In an embodiment, the gram-negative bacterium is *Acinetobacter baumannii* or *Pseudomona aeruginosa*.

In a sixth aspect, this application also provides a polymyxin B component or a salt thereof, where a molecular formula of the polymyxin B component is $C_{56}H_{96}N_{16}O_{13}$, and the polymyxin B component is isolated from polymyxin B or a salt thereof.

In an embodiment, the isolation of the polymyxin B component is from the polymyxin B or a salt thereof is performed by preparative liquid chromatography, where the operations and conditions of the preparative liquid chromatography are the same as those described above.

In a seventh aspect, this application further provides a polymyxin B component or a salt thereof, where the polymyxin B component has a relative molecular weight of 1200.73-1200.75, and the polymyxin B component is isolated from polymyxin B or a salt thereof.

In an embodiment, the isolation of the polymyxin B component from the polymyxin B or a salt thereof is performed by preparative liquid chromatography, and the operations and conditions of the preparative liquid chromatography are the same as those described above.

Compared to the prior art, this application has the following beneficial effects.

1) In this application, individual components of polymyxin B are analyzed online by HPLC-MS and NMR. Based on the analysis of the obtained primary mass spectrum, secondary mass spectrum NMR spectrum, a polymyxin B component including double bond 2',3'-dehydropolymyxin B1 is first identified, which is conducive to the subsequent researches of polymyxin B.

2) The 2',3'-dehydropolymyxin B1 characterized herein has a strong antimicrobial activity, and thus has a brilliant application prospect. Moreover, the level of the 2',3'-dehydropolymyxin B1 can be used as an indicator to evaluate the quality of polymyxin B.

BRIEF DESCRIPTION OF THE DRAWINGS

FIGS. 3a-3b are primary mass spectrums of the polymyxin B1, where FIG. 3b is a partial enlarged view of FIG. 3a.

FIGS. 5a-5b are primary mass spectrums of the 2',3'-dehydropolymyxin B1, where FIG. 5b is a partial enlarged view of FIG. 5a.

DETAILED DESCRIPTION OF EMBODIMENTS

This disclosure will be further described in detail below with reference to the embodiments, and these embodiments are not intended to limit the scope of this disclosure.

Figure 1:
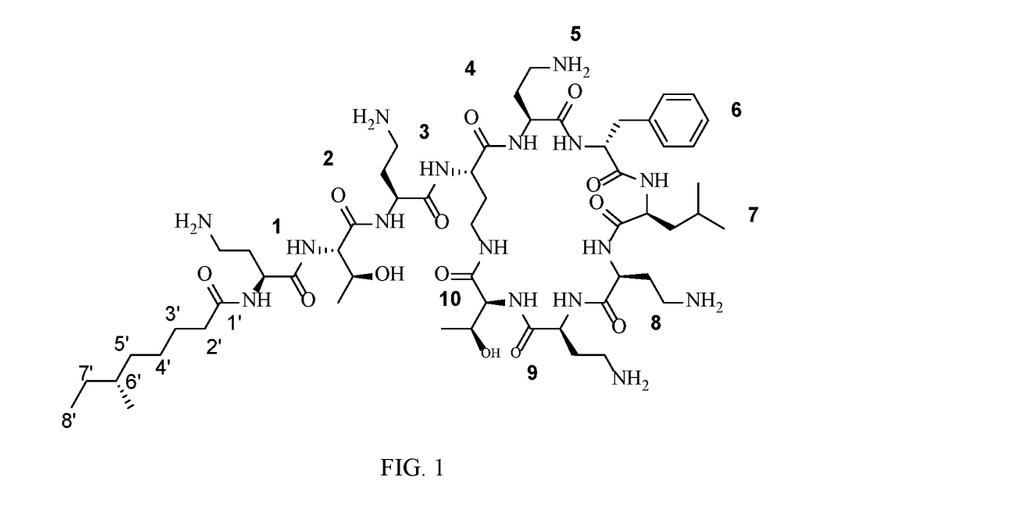
FIG. 1 shows a structural formula of polymyxin B1.

As used herein, the "position 1", "position 2"... "position 10" refer to an order in which the amino acids are linked, and this order is identical to the numerical order revealed in FIG. 1.

As used herein, the "α-amino" and the "γ-amino" refer to an amino linked to an α-carbon atom and a γ-carbon atom, respectively.

In the following examples, the polymyxin B sulfate is purchased from SPH No. 1 BIOCHEMICAL & PHARMACEUTICAL Co., Ltd. It should be understood that other polymyxin B sulfate references or preparations, from which the polymyxin B component mentioned herein can be isolated using the above separation method, are also feasible.

*Acinetobacter baumannii* ATCC19606 (Cat. No. 2208[81, DSM 6974]) used herein is purchased from American Type Culture Collection (ATCC).

*Pseudomona aeruginosa* ATCC27853 (Cat. No. Boston 41501) used herein is purchased from American Type Culture Collection (ATCC).

Example 1

1. Instruments and Drugs

Waters AutoPurification System (Waters Corporation (Shanghai)); Freeze Dryer (LABCONCO Corporation, US); HPLC (Agilent 1290)-MS (6550QTOF) (Agilent Technologies, Inc, US); and NMR spectrometer (Bruker, 300 MHz).

The polymyxin B sulfate was purchased from Shanghai Pharma No. 1 Biochemical & Pharmaceutical Co., Ltd (batch number: 1512802).

2. Purification by Preparative Liquid Chromatography

The polymyxin B sulfate was purified using the Waters AutoPurification System. Specifically, the polymyxin B sulfate was first dissolved with a mixture of water and acetonitrile in a volume ratio of 80:20 to a concentration of 10 mg/mL, and the LC conditions were set as follows: chromatographic column: C18 column (19×100 mm, 5 μm); mobile phase: a mixture of a 0.1% (by volume) aqueous formic acid solution and acetonitrile in a volume ratio of 85:15; flow rate: 15 mL/min; injection volume: 500 μL; and detection wavelength: 215 nm. Individual fractions isolated by the preparative liquid chromatography were detected by ESI-MS, and the target polymyxin B component and the polymyxin B1 were collected, where parameters of the ESI-MS were set as follows: scanning mode: ESI(+); mass analyzer: single quadrupole; scanning range (m/z): 100-1250; and cone energy: 35 V. The fractions of the polymyxin B component (m/z 601.4, $[M+2H]^{2+}$) and polymyxin B1 (m/z 602.2, $[M+2H]^{2+}$) were collected 200 times and combined, respectively. Then the two kinds of fractions were subjected to rotary evaporation to remove the solvent, added with 3-4 mL of water, transferred to a glass bottle and subjected to freeze drying by a freeze dryer, where in the freeze-drying process, a temperature in the cold trap was −80° C.; a vacuum degree was 0 mbar; and after 24 h, when a white flaky and fluffy solid appeared in the bottle, the freeze drying was stopped.

3. MS Analysis of the Polymyxin B1 and the Target Polymyxin B Component

Approximately 2 mg of the purified polymyxin B1 and target polymyxin B component were respectively dissolved in 1 mL of a mixture of water and acetonitrile in a volume ratio of 80:20 and then subjected to structural characterization by HPLC-ESI-Q-TOF MS, where the LC conditions were listed as follows: chromatographic column: C18 column (4.6×250 mm, 5 μm); mobile phase: a mixture of a 0.1% (by volume) aqueous trifluoroacetic acid solution and acetonitrile in a volume ratio of 80:20; flow rate: 1 mL/min; injection volume: 20 μL; detection wavelength: 215 nm; and column temperature: 50° C.; the MS conditions were described as follows: a primary mass spectrum and a secondary mass spectrum were obtained in ESI (+) scanning mode; injection volume: 5 μL; scanning range (m/z); 50-1700; and collision energy of the secondary mass spectrum: 10-30 eV.

Figure 3A:
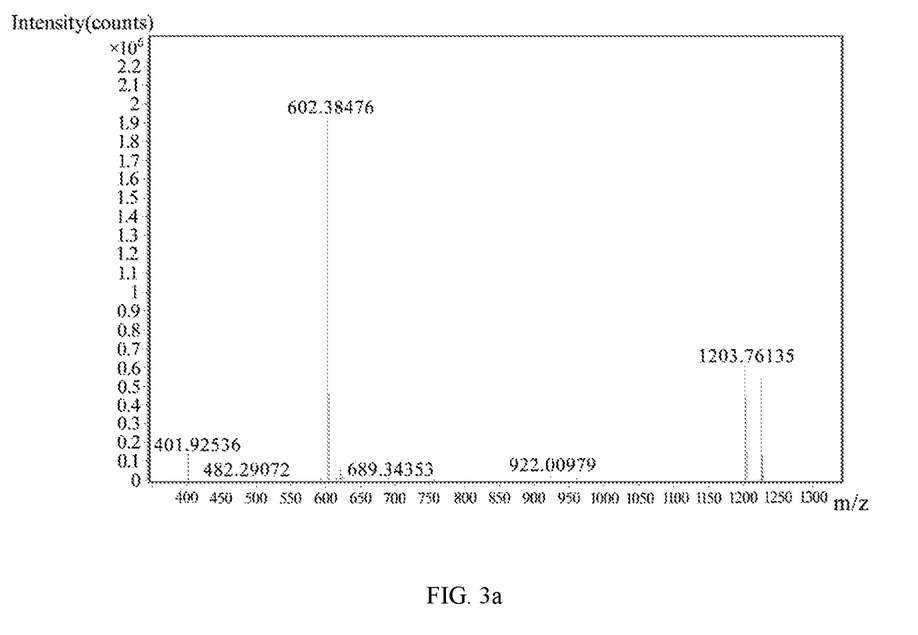
Figure 3B:
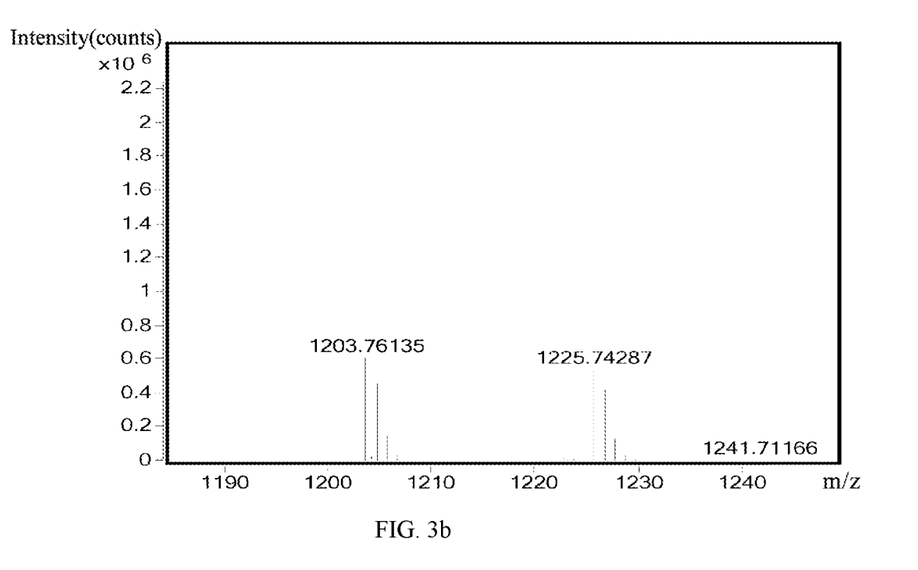
Figure 4:
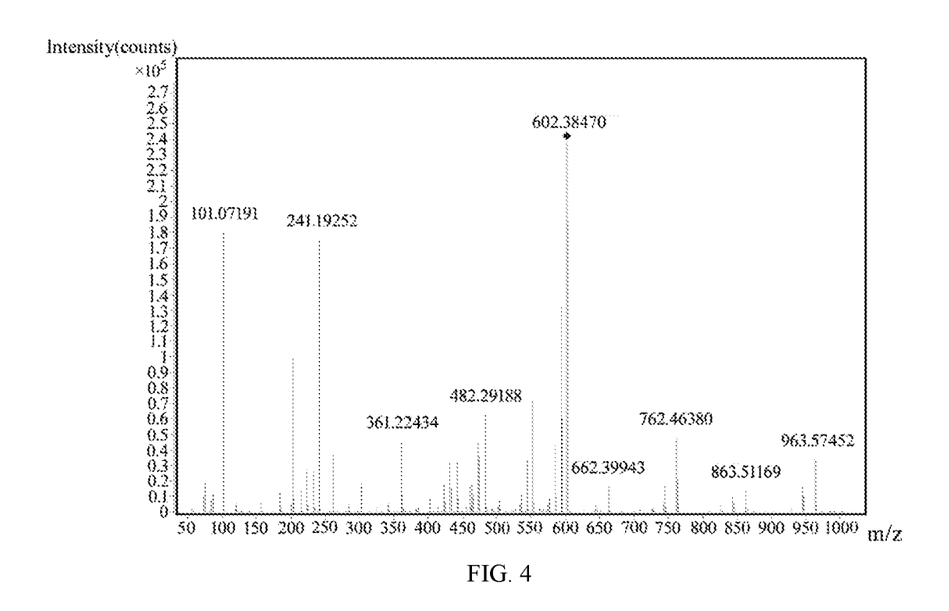
FIG. 4 is a secondary mass spectrum of the polymyxin B1.

The primary mass spectrum of the polymyxin B1 was shown in FIGS. 3a and 3b, in which pseudo-molecular ion peaks $[M+H]^+$ and $[M+Na]^+$ were observed at m/z=1203.7614 and m/z=1225.7429, respectively. In a solution or in the electrospray-ionization process, the polymyxin B1 was prone to forming an adduct ion $[M+2H]^{2+}$ with two H+, which had a peak at m/z=602.3848. Then the $[M+2H]^{22+}$ was used as parent ion and fragmented under an adjusted fragmentor voltage to obtain a secondary mass spectrum of the polymyxin B1 (as shown in FIG. 4), in which characteristic ions were identified at m/z=963.5745, 863.5117, 762.4638, 662.3994, 482.2919, 361.2243, 241.1925 and 101.0719, respectively. Based on these characteristic ions, the order in which the amino acids were linked to constitute the polymyxin B1 can be inferred. Then a comparison was made between the polymyxin B1 and the target polymyxin B component with respect to the characteristic ions to analyze their differences in structure.

Figure 5A:
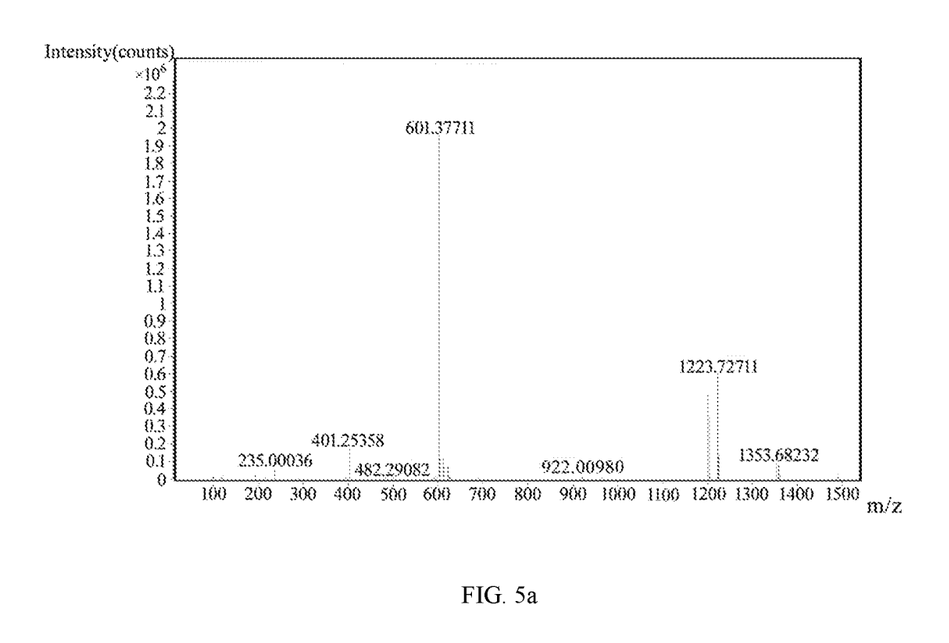
Figure 5B:
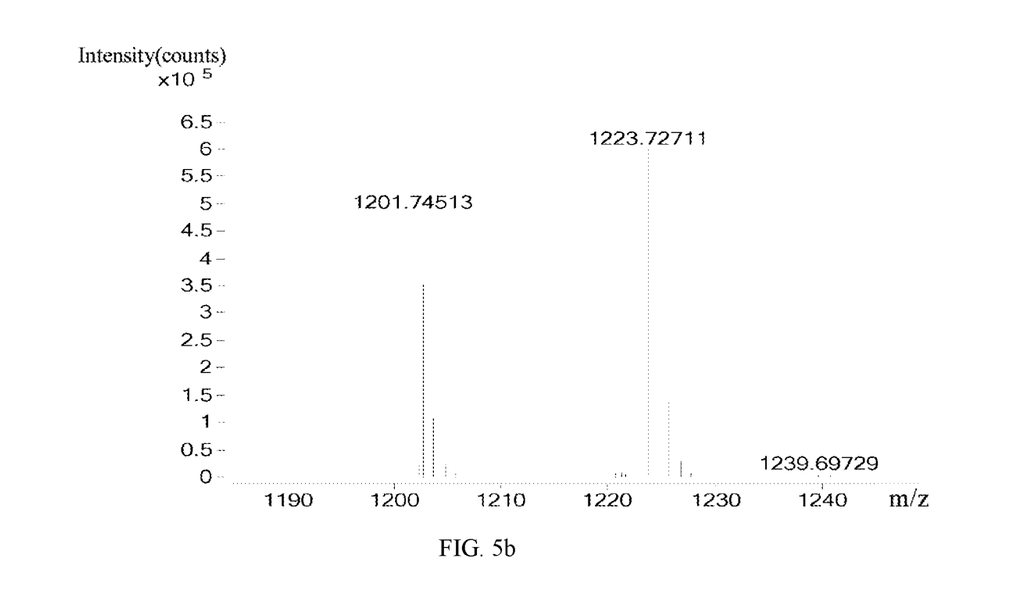
Figure 6:
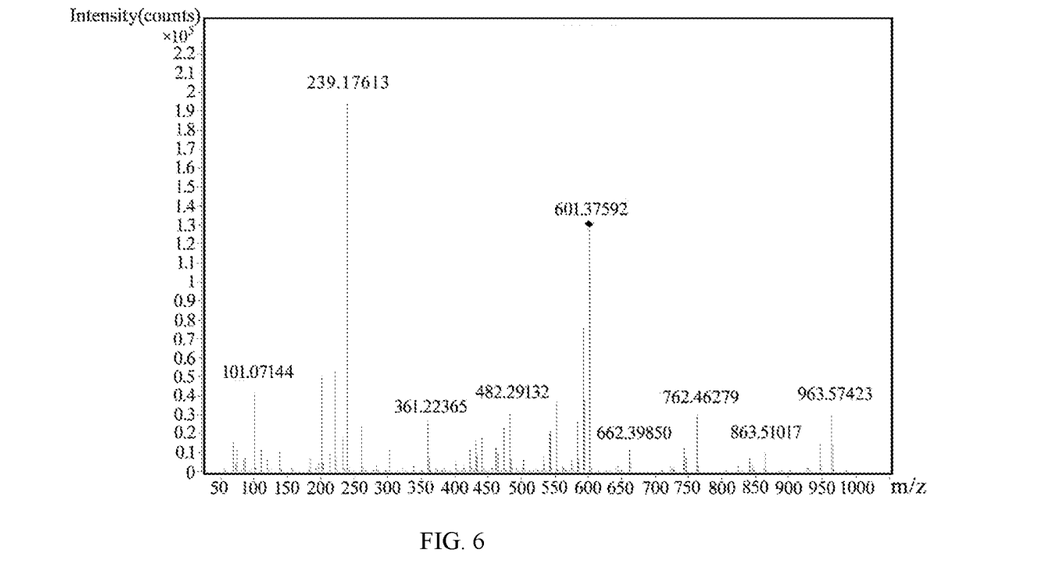
FIG. 6 is a secondary mass spectrum of the 2',3'-dehydropolymyxin B1.

The primary mass spectrum of the target polymyxin B component was shown in FIGS. 5a and 5b, in which pseudo-molecular ion peaks $[M+H]^+$ and $[M+Na]^+$ were observed at m/z=1201.7451 and m/z=1223.7271, respectively, and an adduct ion $[M+2H]^{2+}$ was observed at m/z=601.3771. Then the $[M+2H]^{2+}$ was used as parent ion and fragmented under an adjusted fragmentor voltage to obtain a secondary mass spectrum of the target polymyxin B component (as shown in FIG. 6), in which characteristic ions were identified at m/z=963.5742, 863.5102, 762.4628, 662.3985, 482.2913, 361.2237, 239.1761 and 101.0714. The target polymyxin B component was structurally characterized based on the information of the primary and secondary mass spectrums. By comparison, the characteristic ion 239.1761 of the target polymyxin B component was about 2 smaller than the characteristic ion 241.1925 of the polymyxin B1 in m/z, based on which it can be deduced that a double bond occurred on the N-terminal fatty acyl chain. Therefore, the target polymyxin B component was referred to as 2',3'-dehydropolymyxin B1.

The mass spectrum showed that the 2',3'-dehydropolymyxin B1 included six α,γ-diaminobutyric acids respectively at positions 1, 3-4 and 8-9, two threonine residues at positions 2 and 10, a phenylalanine residue at position 6 and a leucine residue at position 7 linked in sequence, where the threonine residue at position 10 was linked to the α,γ-diaminobutyric acid at position 4 through an amido bond, and the α,γ-diaminobutyric acid at position 1 was linked to 6-methyloctyl-2-enoyl. The target polymyxin B component had a molecular formula of $C_{56}H_{96}N_{16}O_{13}$.

It can be determined according to the existing data (referring to European Pharmacopoeia 9.7; polymyxin B sulfate, page: 6668-6669; ORWAJ A, et. al., J Chromatogr A, 2001, 912 (2):369-373; GOVAERTS C, et. al., J Peptide Sci, 2002, 8(2):45-55) that an α-amino of the α,γ-diaminobutyric acid at position 1 was linked to (R,E)-6-methyloctyl-2-enoyl, (R,Z)-6-methyloctyl-2-enoyl, or an enantiomer thereof; a carboxyl of the α,γ-diaminobutyric acid at position 1 was linked to an amino of the threonine residue at position 2; a carboxyl of the threonine residue at position 2 was linked to an α-amino of the α,γ-diaminobutyric acid at position 3; a carboxyl of the α,γ-diaminobutyric acid at position 3 was linked to an α-amino of the α,γ-diaminobutyric acid at position 4; a carboxyl of the α,γ-diaminobutyric acid at position 4 was linked to an α-amino of the α,γ-diaminobutyric acid at position 5; a carboxyl of the α,γ-diaminobutyric acid at position 5 was linked to an amino of the phenylalanine residue at position 6; a carboxyl of the phenylalanine residue at position 6 was linked to an amino of the leucine residue at position 7; a carboxyl of the leucine residue at position 7 was linked to an α-amino of the α,γ-diaminobutyric acid at position 8; a carboxyl of the α,γ-diaminobutyric acid at position 8 was linked to an α-amino of the α,γ-diaminobutyric acid at position 9; a carboxyl of the α,γ-diaminobutyric acid at position 9 was linked to an amino of the threonine residue at position 10; and ay-amino of the α,γ-diaminobutyric acid at position 4 was linked to a carboxyl of the threonine residue at position 10 through an amide bond to form a cyclic heptapeptide.

4. NMR Analysis of Polymyxin B1 and 2',3'-dehydropolymyxin B1

Figure 7:
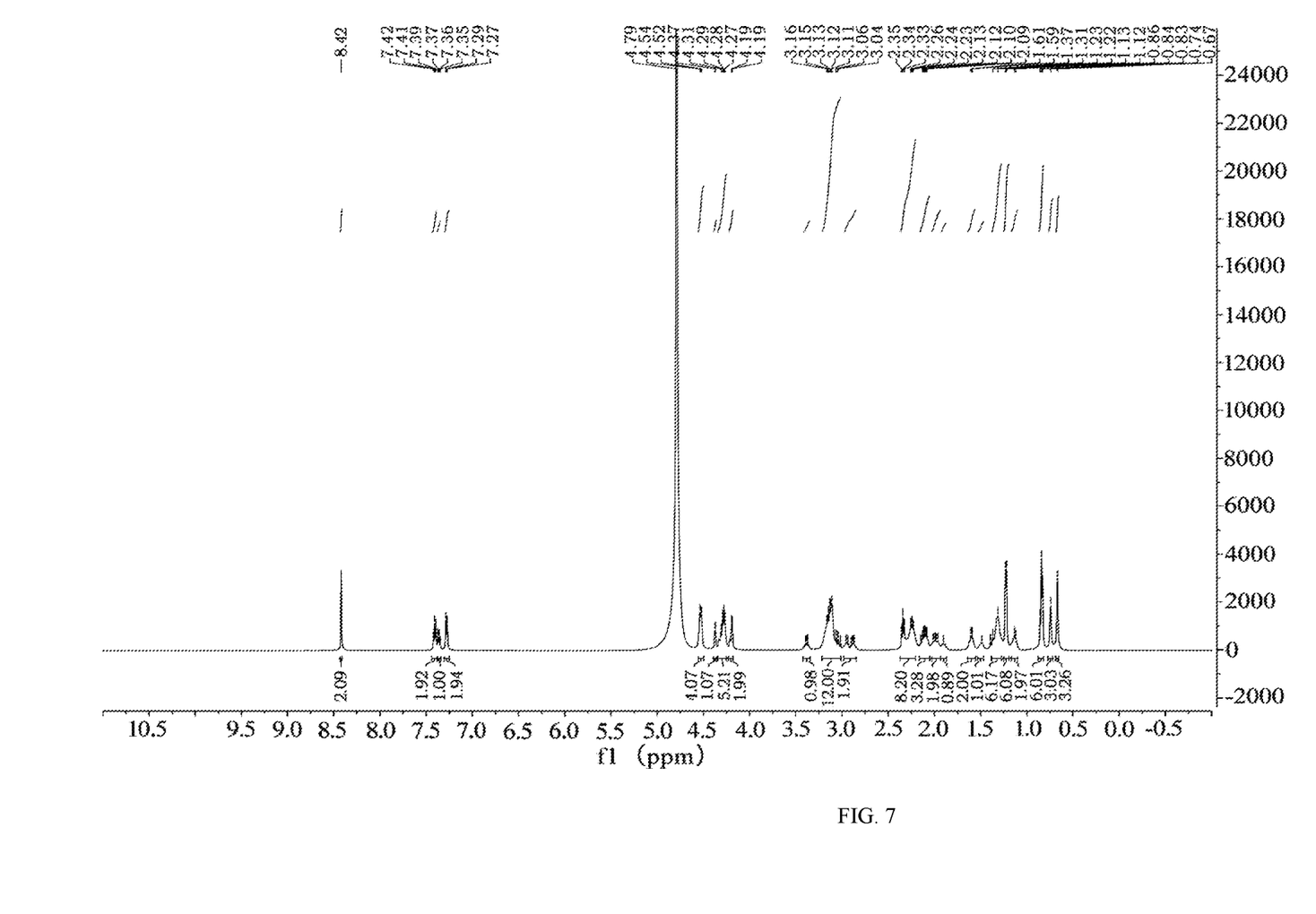
FIG. 7 is an H-NMR spectrum of the polymyxin B1.
Figure 8:
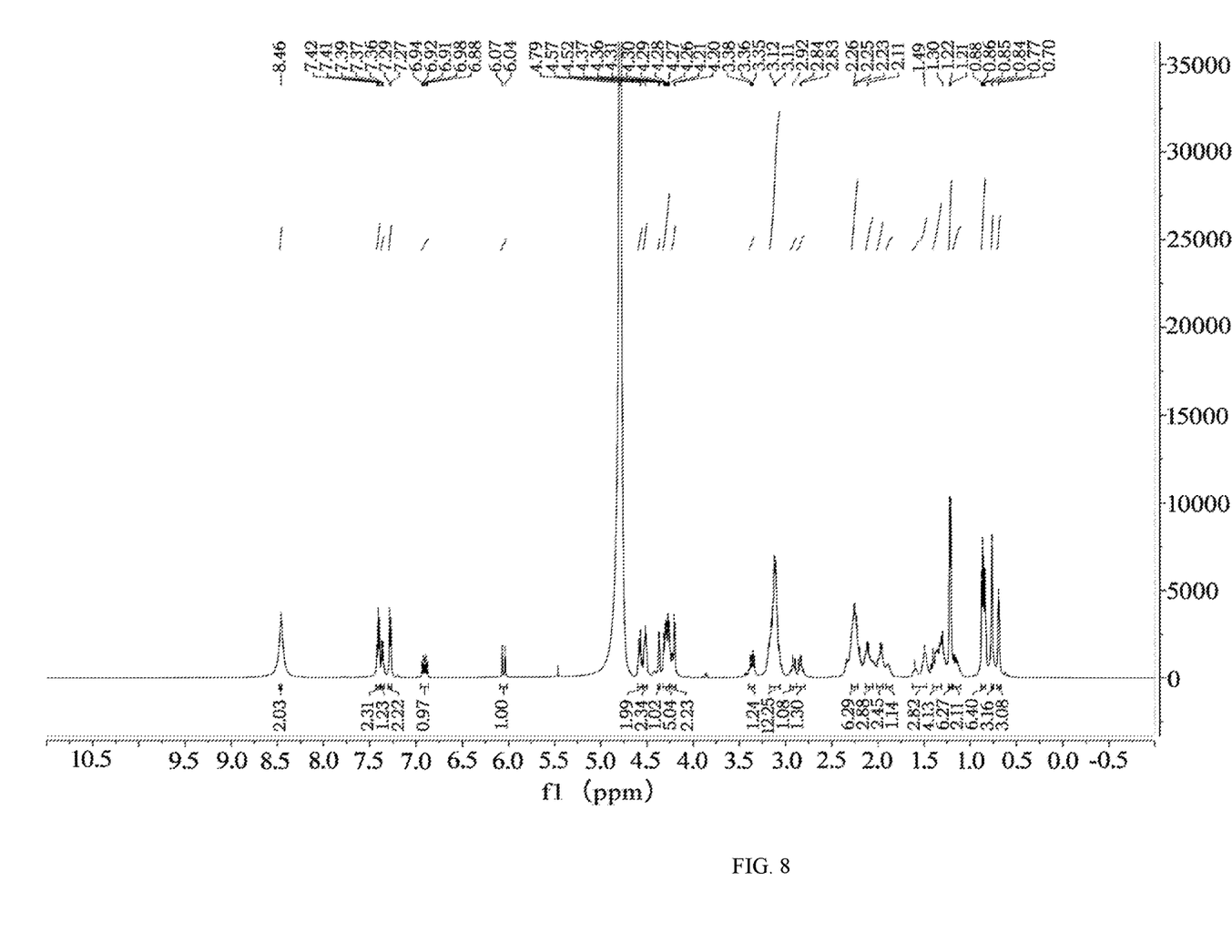
FIG. 8 is an H-NMR spectrum of the 2',3'-dehydropolymyxin B1.

Approximately 2 μmg of the purified polymyxin B1 and the 2',3'-dehydropolymyxin B1 were respectively dissolved in deuterium water, transferred to an NMR tube and analyzed by NMR spectrometer for H-NMR spectrum, where the H-NMR spectrums of the polymyxin B1 and the 2',3'-dehydropolymyxin B1 were presented in FIG. 7 and FIG. 8, respectively. By contrast, the difference between the two H-NMR spectrums mainly existed in the chemical shift of 6-7, where the chemical shifts of 6.05 (d, J=15.4 Hz, 1H) and 6.91 (dt, J=15.4, 7.6 Hz, 1H) indicated characteristic peaks of the double bond (2' hydrogen and 3' hydrogen). Moreover, since the cis double bond generally had a coupling constant of about 10.9 Hz, the double bond with a coupling constant of 15.4 Hz in the 2',3'-dehydropolymyxin B1 was considered as a trans double bond. Considering that the separate double bond had a chemical shift of 5-6, and the double bond hydrogen will shift to a chemical shift of 6-7 after conjugated with a carbonyl, it can be deduced from the chemical shift of the lower field that the double bond and the carbonyl group formed a conjugated structure.

Figure 2:
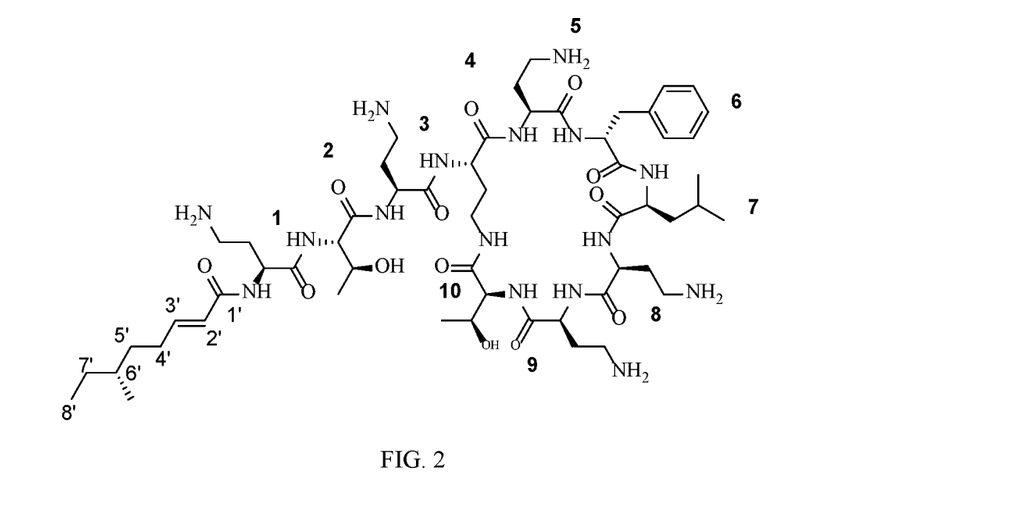
FIG. 2 depicts a structural formula of 2',3'-dehydropolymyxin B1.

The configuration of the chiral carbon of the target component can be determined according to the data in the above-mentioned pharmacopoeia and literatures, and the structure of the target polymyxin B component was shown in FIG. 2.

5. Determination of Antibacterial Activity of Polymyxin B1 and 2',3'-dehydropolymyxin B1

Minimal inhibitory concentrations (MIC) of the polymyxin B1 (PMB1) and the 2',3'-dehydropolymyxin B1 against *Acinetobacter baumannii* were determined using a microdilution broth method as instructed by Clinical & Laboratory Standards Institute (CLSI). Specifically, *Acinetobacter baumannii* ATCC19606 (standard strain) was inoculated into a 96-well plate at a density of 10 CFU/mL, to which a PMB1 solution (as control) or a 2',3'-dehydropolymyxin B1 solution was added to a series of final concentrations of 0.125, 0.25, 0.5, 1, 2, 4 and 8 mg/L. The 96-well plate was incubated at 35±2° C. for 18-24 h, and then observed for the turbidity in each test well, where the lowest concentration of PMB1 or 2',3'-dehydropolymyxin B1 under which the system in the test well became clear was considered as the corresponding MIC. The results were shown in Table 1.

TABLE 1

MIC of polymyxin B1 and 2',3'-dehydropolymyxin B1 against *Acinetobacter baumannii*

| Strain | MIC (mg/L) | |
|---|---|---|
| | Polymyxin B1 | 2',3'-dehydropolymyxin B1 |
| ATCC19606 | 1 | 0.5 |

It can be concluded from Table 1 that the 2',3'-dehydropolymyxin B1 had an antibacterial activity against the *Acinetobacter baumannii* ATCC19606, and the MIC of the 2',3'-dehydropolymyxin B1 was one dilution lower than that of the polymyxin B1 (the error tolerance of this method was 1 dilution), indicating that the 2',3'-dehydropolymyxin B1 was superior to the polymyxin B1 in antibacterial activity.

Furthermore, the polymyxin B1 (PMB1) and the 2',3'-dehydropolymyxin B1 were also determined for MIC against *Pseudomona aeruginosa* using the microdilution broth method as instructed by CLSI. Similarly, the *Pseudomona aeruginosa* ATCC27853 (standard strain) was inoculated into a 96-well plate at a density of 106 CFU/mL, to which a PMB1 solution (as control) or a 2',3'-dehydropolymyxin B1 solution was added to a series of final concentrations of 0.125, 0.25, 0.5, 1, 2, 4 and 8 mg/L. The 96-well plate was incubated at 352° C. for 18-24 h, and then observed for the turbidity in each test well, where the lowest concentration of PMB1 or 2',3'-dehydropolymyxin B1 under which the system in the test well became clear was considered as the corresponding MIC. The results were shown in Table 2.

TABLE 2

MIC of polymyxin B1 and 2',3'-dehydropolymyxin B1 against *Pseudomona aeruginosa*

| Strain | MIC (mg/L) | |
|---|---|---|
| | Polymyxin B1 | 2',3'-dehydropolymyxin B1 |
| ATCC27853 | 1 | 1 |

The results demonstrated that the 2',3'-dehydropolymyxin B1 had an antibacterial activity against the *Pseudomona aeruginosa* ATCC278533, and the MIC of the 2',3'-dehydropolymyxin B1 was similar to that of the polymyxin B1, indicating the 2',3'-dehydropolymyxin B1 was equivalent to the polymyxin B1 in the antibacterial activity against the *Pseudomona aeruginosa*.

In summary, a new polymyxin B component (2',3'-dehydropolymyxin B1) is first found and characterized herein by preparative LC, HPLC-MS and NMR. Moreover, this component with a double bond has excellent antibacterial activity and biological activity, having considerable potential in the clinical treatment.

It should be noted that the above-mentioned embodiments are only illustrative of this disclosure, and are not intended to limit the scope of the disclosure. Any improvement, adjustment and modification made by those of ordinary skill in the art without departing from the spirit of the disclosure shall fall within the scope of the disclosure.

What is claimed is:

1. A method for preparing a polymyxin B component, a molecular formula of the polymyxin B component being $C_{56}H_{96}N_{16}O_{13}$, the method comprising:
   isolating the polymyxin B component from polymyxin B or a salt thereof by preparative liquid chromatography;
   wherein a chromatographic column used in the preparative liquid chromatography is a C18 column;
   a mobile phase used in the preparative liquid chromatography is a mixture of an aqueous formic acid solution and acetonitrile, where a volume percentage of formic acid in the aqueous formic acid solution is greater than 0 and less than or equal to 10%;
   a volume ratio of the aqueous formic acid solution to acetonitrile is (99-1):1;
   a flow rate of the mobile phase is 5-20 mL/min; an injection volume is 50-1000 µL; and a detection wavelength is 190-400 nm;
   individual fractions separated by the preparative liquid chromatography are detected by the ESI-MS and the polymyxin B component of interest is collected; and
   the ESI-MS is performed in a positive ion mode with a scanning range (m/z) of 50-3200.

2. The method of claim 1, wherein the volume percentage of formic acid in the aqueous formic acid solution is 0.01%-10%;
   the volume ratio of the aqueous formic acid solution to acetonitrile is 85:15;
   the flow rate of the mobile phase is 15 mL/min;
   the injection volume is 500 µL;
   the detection wavelength is 215 nm;
   the scanning range (m/z) is 100-1250.

3. The method of claim 2, wherein the volume percentage of formic acid in the aqueous formic acid solution is 0.1%.

4. A method for preparing a salt of a polymyxin B component, a molecular formula of the polymyxin B component being $C_{56}H_{96}N_{16}O_{13}$, the method comprising:

isolating the polymyxin B component from polymyxin B or a salt thereof by preparative liquid chromatography; and subjecting the polymyxin B component to salt formation with an acid to produce the salt of the polymyxin B component;

wherein a chromatographic column used in the preparative liquid chromatography is a C18 column;

a mobile phase used in the preparative liquid chromatography is a mixture of an aqueous formic acid solution and acetonitrile, where a volume percentage of formic acid in the aqueous formic acid solution is greater than 0 and less than or equal to 10%;

a volume ratio of the aqueous formic acid solution to acetonitrile is (99-1):1;

a flow rate of the mobile phase is 5-20 mL/min; an injection volume is 50-1000 µL; and a detection wavelength is 190-400 nm;

individual fractions separated by the preparative liquid chromatography are detected by the ESI-MS and the polymyxin B component of interest is collected; and the ESI-MS is performed in a positive ion mode with a scanning range (m/z) of 50-3200.

5. The method of claim 4, wherein the volume percentage of formic acid in the aqueous formic acid solution is 0.01%-10%;

the volume ratio of the aqueous formic acid solution to acetonitrile is 85:15;

the flow rate of the mobile phase is 15 mL/min;

the injection volume is 500 µL;

the detection wavelength is 215 nm;

the scanning range (m/z) is 100-1250.

6. The method of claim 5, wherein the volume percentage of formic acid in the aqueous formic acid solution is 0.1%.

* * * * *